(12) United States Patent
Fischer et al.

(10) Patent No.: US 6,746,689 B2
(45) Date of Patent: *Jun. 8, 2004

(54) INTRADERMAL-PENETRATION AGENTS FOR TOPICAL LOCAL ANESTHETIC ADMINISTRATION

(75) Inventors: Wilfried Fischer, Neubiberg (DE); Petra Huber, Munich (DE); Paul Mason, Flemington, NJ (US)

(73) Assignee: EpiCept Corporation, Englewood Cliff, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/201,901

(22) Filed: Jul. 25, 2002

(65) Prior Publication Data

US 2003/0138505 A1 Jul. 24, 2003

Related U.S. Application Data

(63) Continuation of application No. 09/523,652, filed on Mar. 10, 2000, now Pat. No. 6,455,066.

(51) Int. Cl.$^7$ ............................................. A61K 35/78
(52) U.S. Cl. .................... 424/449; 424/744; 424/757; 424/774; 424/778; 424/447; 424/448; 514/646
(58) Field of Search .................. 424/774, 757, 424/778, 447, 448, 449; 514/646

(56) References Cited

U.S. PATENT DOCUMENTS

| | | |
|---|---|---|
| 3,814,095 A | 6/1974 | Lubens |
| 3,892,853 A | 7/1975 | Cobble |
| 4,210,670 A | 7/1980 | Cooke |
| 4,748,022 A | 5/1988 | Busciglio |
| 4,765,986 A | 8/1988 | Liedtke |
| 4,917,688 A | 4/1990 | Nelson et al. |
| 5,002,974 A | 3/1991 | Geria |
| 5,120,710 A | 6/1992 | Liedtke |
| 5,229,130 A | 7/1993 | Sharma et al. |
| 5,272,139 A | 12/1993 | Cary, Jr. |
| 5,279,837 A | 1/1994 | Hill |
| 5,330,452 A | 7/1994 | Zook |
| 5,332,576 A | 7/1994 | Mantelle |
| 5,356,811 A | 10/1994 | Coats |
| 5,411,738 A | 5/1995 | Hind |
| 5,415,866 A | 5/1995 | Zook |
| 5,466,465 A | 11/1995 | Royds et al. |
| 5,589,180 A | 12/1996 | Hind |
| 5,720,962 A | 2/1998 | Ivy et al. |
| 5,776,952 A | 7/1998 | Liedtke |
| 5,810,786 A | 9/1998 | Jackson et al. |
| 5,827,529 A | 10/1998 | Ono et al. |
| 5,840,755 A | 11/1998 | Liedtke |
| 5,863,941 A | 1/1999 | Liedtke |
| 5,919,479 A | 7/1999 | Zhang et al. |
| 5,922,340 A | 7/1999 | Berde et al. |
| 5,955,112 A | 9/1999 | Kaplan |
| 6,120,792 A | 9/2000 | Juni |
| 6,455,066 B1 * | 9/2002 | Fischer et al. |

FOREIGN PATENT DOCUMENTS

| | | |
|---|---|---|
| WO | WO 93/12744 | 7/1993 |
| WO | WO 95/31188 | 11/1995 |
| WO | WO 97/43989 | 11/1997 |
| WO | WO 00/30694 | 6/2000 |
| WO | WO 01/41745 | 6/2001 |
| WO | WO 01/41746 | 6/2001 |

OTHER PUBLICATIONS

Berkovitch et al., 1995, "Use of a Eutectic Mixture of Local Anesthetics for Prolonged Subcutaneous Drug Administration", J. Clin. Pharmacol. 35:295–297.

Curatolo, 1987, "The Lipoidal Permeability Barriers of the Skin and Alimentary Tract", Pharmaceut. Res. 4:271–277.

Klein and Penneys, 1988, "Aloe Vera", J. Am. Acad. Dermatol. 18:714–720.

Lubens et al., 1974, "Anesthetic Patch for Painful Procedures Such As Minor Operations", Am. J. Dis. Child. 128:192–194.

McCafferty et al., 1988, "Comparative in vivo and in vitro Assessment of the Percutaneous Absorption of Local Anesthetics", Br. J. Anaesth. 60:64–69.

Russo et al., 1980, "Lidocaine Anesthesia: Comparison of Iontophoresis, Injection and Swabbing", Am. J. Hosp. Pharm. 37:843–847.

Sarpotdar and Zatz, 1986, "Evaluation of Penetration Enhancement of Lidocaine by Nonionic Surfactants Through Hairless Mouse Skin In Vitro", J. Pharmaceut. Sci. 75:176–181.

Shelton, 1991, "Aloe Vera: Its Chemical and Therapeutic Properties", Intl. J. Dermatol. 30:679–683.

Takahashi et al., "In vitro Transport of Sodium Diclofenac across Rat Abdominal Skin: Effect of Selection of Oleaginous Component and the Addition of Alcohols to the Vehicle", Chem. Pharm. Bull. 39:154–158.

Wang and Strong, 1993, "Monitoring Physical and Chemical Properties of Freshly Harvested Field–Grown *Aloe vera* Leaves. A Preliminary Report", Phytotherapy Res. 7:S1–S4.

* cited by examiner

Primary Examiner—Leon B. Lankford, Jr.
Assistant Examiner—Susan D. Coe
(74) Attorney, Agent, or Firm—Jones Day

(57) ABSTRACT

A non-invasive and non-systemic method for administering a local anesthetic. The method comprises topical application of a local anesthetic in combination with an intradermal-penetration agent selected from the group consisting an aloe composition, a triglyceride, and a mixture thereof.

11 Claims, No Drawings

INTRADERMAL-PENETRATION AGENTS FOR TOPICAL LOCAL ANESTHETIC ADMINISTRATION

This is a continuation of application Ser. No. 09/523,652, filed Mar. 10, 2000, now U.S. Pat. No. 6,455,066.

FIELD OF THE INVENTION

The invention relates to methods and compositions for intradermal administration of local anesthetics with the aid of an intradermal-penetration agent.

BACKGROUND OF THE INVENTION

Drug administration by topical skin application offers distinct advantages over conventional administration methods. For example, some drugs cannot be absorbed in the digestive tract and intravenous and subcutaneous administration by injection is painful and invasive. Furthermore, when treating localized conditions by oral and intravenous administration, the drug is circulated systemically rather than restricted to the diseased area.

But, unfortunately, because of the skin's drug penetration resistance, only a limited number of drugs are bioavailable via topical application (Ghosh, T. K.; Pfister, W. R.; Yum, S. I. *Transdermal and Topical Drug Delivery Systems*, Interpharm Press, Inc. p. 7). The skin is a complex multilayer organ with a total thickness of 2–3 mm. The panniculus adiposus, a variably thick fatty layer, is below the dermis. The dermis is a layer of dense connective tissue that supports the epidermis. The epidermis comprises a layer of epithelial cells and is about 100 $\mu$m thick. The epidermis is further classified into a number of layers, of which the outermost layer is the stratum corneum (15–20 $\mu$m thick). The stratum corneum comprises highly dense, keratinized tissue and is the skin's main source of penetration and permeation resistance (Montagna, W. and Parakkal, P. F. (1974) *The Structure and Function of Skin*, Academic Press, New York and Holbrook, K. A. and Wolf, K. (1993) The Structure and Development of Skin, In: *Dermatology in General Medicine*, Vol 1, 4th ed., Eds. T. B. Fitzpatrick, A. Z. Eisen, K. Wolff, I. M. Feedberg, and K. F. Austen, McGraw Hill, Inc., New York, pp. 97–145).

In general, drug administration via the skin is divided into two categories: 1) transdermal administration and 2) intradermal administration. Transdermal administration involves transport through the skin and into the blood stream to treat systemic diseases. One the other hand, intradermal administration is intended to impart a cutaneous effect, while keeping the pharmocological effects of the drug localized to the intracutaneous regions of drug penetration and deposition. Ideally, intradermal absorption occurs with little or no systemic absorption or accumulation.

The following sequence of mechanisms has been proposed for intradermal absorption: 1) partitioning of the drug from the applied vehicle into the stratum corneum; 2) diffusion through the stratum corneum; 3) partitioning from the stratum into the epidermis. On the other hand, transdermal absorption further involves: 4) diffusion through the epidermis; and 5) capillary uptake (Potts et al. (1992) *Percutaneous Absorption: Pharmacology of the Skin*, Ed. Mukhtar, H. CRC Press, pp. 13–27).

Because of the skins intrinsic resistance to drug penetration, penetration agents are essential to assist intradermal and transdermal drug administration. The term penetration agent has generally been applied to the class of chemicals that increase the partitioning and diffusion of the active agent. (for example see, Ghosh, T. K. et al. (1993), *Pharm. Tech.* 17(3):72–98; Ghosh, T. K. et al. (1993), *Pharm. Tech.* 17(4): 62–89; Ghosh, T. K. et al. (1993), *Pharm. Tech.* 17(5):68–76; Pfister et al. *Pharm. Tech.* 14(9):132–140, all of are incorporated herein by reference). Ideally penetration agents should be pharmacologically inert, non-toxic, non-irritating and non-allergenic, compatible with the formulation components, have rapid onset of action, and be reversible in their reduction of skin-barrier properties. The penetration agent should also spread well on the skin with a suitable skin feel. In practice, all of these ideal requirements are rarely met, and a need exists for improved penetration agents. (Aungst (1991) *Skin Permeation Enhancers for Improved Transdermal Drug delivery. In: High Performance Biomaterial: A Comprehensive Guide to Medical and Pharmaceutical Applications*, Ed. M. Szycher, pp. 527–538)).

The majority of dermal drug formulations and penetration agents for have been developed for transdermal administration. For example, U.S. Pat. No. 5,229,130 relates to the use of vegetable oils to enhance transdermal penetration of drugs through the skin into the blood stream. U.S. Pat. No. 5,229,130 teaches that vegetable oils (e.g., almond oil, babassu oil, castor oil, Clark A oil, coconut oil, corn oil, cotton seed oil, jojoba oil, linseed oil, mustard oil, olive oil, palm oil, peanut oil, safflower oil, sesame oil, soybean oil, sunflower-seed oil and wheat germ oil) as transdermal penetration agents for broad classes of pharmaceutically active compounds amenable to transdermal administration (e.g., antiinfectives; analgesics; anorexics; antihelminthics; antiarthritics; antiasthmatics; anticonvulsants; antidepressants; antidiabetics; antidiarrheals; antihistamines; antiinflammatories; antimigraine preparations; and tranquilizers).

Although transdermal systems can deliver drugs for the treatment of systemic disease, they are not practical for controlling the administration of drugs when the skin is the target site (i.e., intradermal administration). The controlled release of drugs into the epidermis or dermis, with the assurance that the drug remains primarily localized and does not enter the blood stream in significant amounts requires innovative approaches ((Ghosh, T. K.; Pfister, W. R.; Yum, S. I. (1997) *Transdermal and Topical Drug Delivery Systems*, p. 521)). Further complicating the matter, the behavior of a penetration agent is strongly dependant on the drug. That is, a given penetration agent does not necessarily increase the penetration of all drugs (Hori et al. (1989) Classification of *Percutaneous Absorption: Mechanisms-Methodology-Drug Delivery*, 2nd ed., Eds. R. L. Bronaugh and H. I. Maibach pp. 197–211).

Certain aesthetics are advantageous for local administration. Especially amide and ester type local anesthetics (e.g., lidocaine, tetracaine, bupivacaine, prilocaine, mepivacaine, procaine, chloroprocaine, ropivacaine, dibucaine, etidocaine, and benzocaine). Traditionally, pain relief with local anesthetics involves injection into the area of the nerve fibers to be blocked (Jones M. Gregg A K, Anaesthesia February 1999; 54(2):200). While topical application of local anesthetics might overcome the disadvantages associated with injection (especially systemic dangers), this method has not been widely used, mainly, as discussed above, because of the difficulty to get significant concentrations of local anesthetics through skin barrier. But if a penetration agent is used, the danger of systemic absorption increases and this is significant because amide and ester anesthetics are systemically toxic.

Thus a need exists for penetration agents for intradermal local anesthetic administration. The agent should have balanced penetration properties such the intradermal penetration is maximized and transdermal penetration is minimized. Additionally, the agent should be pharmacologically inert, non-toxic, non-irritating and non-allergenic, compatible with the formulation components, have rapid onset of action, and spread well on the skin with a suitable skin feel.

SUMMARY OF THE INVENTION

It has now been found that triglycerides and aloe compositions are intradermal-penetration agents for enhancing penetration of topically applied local anesthetics through the stratum corneum and into the epidermis or dermis, in the absence of systemic absorption of the anesthetic.

In one embodiment, the invention comprises a method for administering a local anesthetic in a subject in need of a local anesthetic. The method comprises applying to the subject's skin a pharmaceutically acceptable topical formulation comprising a therapeutically effective amount of the local anesthetic or a pharmaceutically acceptable salt thereof and a penetration enhancing amount of an intradermal-penetration agent selected from the group consisting of a triglyceride, an aloe composition, and a mixture thereof. In another embodiment, the pharmaceutically acceptable topical formulation is in a patch. Preferably, there is no significant systemic absorption of the local anesthetic. One indicator of non-systemic absorption is that the duration of local anesthesia imparted by a local anesthetic augmented with a triglyceride is about the same as that without the triglyceride. In essence, the duration of a local anesthetic effect augmented by the penetration properties of a triglyceride is equivalent to that without the triglyceride, but, advantageously, the effect is more intense, thereby, allowing for greater efficacy of treatment. This is surprising because higher local anesthetic intensity would be expected to be accompanied by greater systemic absorption.

In still another embodiment, the invention relates to a patch comprising a penetration enhancing amount of an intradermal-penetration agent selected from the group consisting of a triglyceride, an aloe composition, and a mixture thereof and a therapeutically effective amount of a local anesthetic to administer the local anesthetic in a subject in need of a local anesthetic effect packaged in association with instructions, the instructions comprising: applying the patch to the skin.

In yet another embodiment, the invention relates to a patch comprising a backing and a pressure sensitive acrylic adhesive, which adhesive comprises a therapeutically effective amount of a local anesthetic and a penetration enhancing amount of an intradermal-penetration agent selected from the group consisting of a triglyceride, an aloe composition, and a mixture thereof.

In another embodiment, the invention relates to a composition comprising a therapeutically effective amount of a local anesthetic or a pharmaceutically acceptable salt thereof and a penetration enhancing amount of an intradermal-penetration agent selected from the group consisting of a triglyceride, an aloe composition, and a mixture thereof.

These and other features, aspects, and advantages of the invention will become better understood with reference to the following detailed description, example, and appended claims.

DETAILED DESCRIPTION OF THE INVENTION

In one embodiment, the invention comprises a method for administering a local anesthetic in a subject in need of a local anesthetic effect comprising applying to the subject's skin a pharmaceutically acceptable topical formulation comprising a therapeutically effective amount of the local anesthetic or a pharmaceutically acceptable salt thereof and a penetration enhancing amount of an intradermal-penetration agent selected from the group consisting of a triglyceride, an aloe composition, and a mixture thereof.

As used herein the term "intradermal-penetration agent" means an agent capable of transporting a pharmacologically active compound through the stratum corneum and into the epidermis or dermis, while keeping the pharmacological effects restricted to the intracutaneous regions of drug penetration, preferably, with little or no systemic absorption. A "penetration enhancing amount" of an intradermal-penetration agent is an amount which enhances the local anesthetic penetration rate through the stratum corneum, relative to the penetration rate without the intradermal-penetration agent. According to the invention, preferred intradermal-penetration agents include triglycerides and aloe compositions.

The term "pharmaceutically acceptable topical formulation" as used herein means any formulation which is pharmaceutically acceptable for intradermal administration of a local anesthetic by application of the formulation to the epidermis. According to the invention, a "topical formulation" will comprise at least a local anesthetic and an intradermal-penetration agent. The choice of topical formulation will depend or several factors, including the condition to be treated, the physicochemical characteristics of the local anesthetic and other excipients present, their stability in the formulation, available manufacturing equipment, and costs constraints.

As used herein, a "therapeutically effective amount of a local anesthetic" means the amount of the anesthetic required to induce a local anesthetic effect sufficient to treat or ameliorate a condition aggravated or induced by stimulation of sub-dermal sensory nerve receptors. Preferably, the local anesthetic does not penetrate through the skin and into the blood stream.

As used herein, the term "subject" means any animal, preferably a mammal, more preferably a human.

As used herein, the term "triglyceride" means any triester of glycerol. Triglycerides useful in the invention are represented by Formula I below:

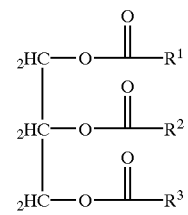

I wherein preferred $R^1$, $R^2$, and $R^3$ groups are independently $C_4$–$C_{24}$ branched or straight chain hydrocarbon groups with zero or more double bonds, preferably $C_{16}$–$C_{20}$ branched or straight chain hydrocarbon groups with zero to three double bonds. Preferably, the triglyceride is derived from a natural source, such as from an animal (e.g., tallow, lard, beef fat, butterfat, and fish oils, such as herring) or a vegetable. Vegetable oils are particularly preferred for use with the invention, for example, but not limited to, nut oils, such as almond oil and walnut oil; castor oil; coconut oil; corn oil; cotton seed oil; jojoba oil; linseed oil; grape seed oil; rape seed oil; mustard oil; olive oil; palm and palm kernel oil; peanut oil; safflower oil; sesame oil; soybean oil; sunflower-seed oil; crambe oil; wheat germ oil; cocoa butter; or mixtures thereof. Soybean oil is a preferred vegetable oil for use with the invention. If desired, the vegetable oils may be processed, for example by hydrogenation.

As used herein, the term "aloe composition" means any extract or processed form of a plant of genus aloe, family Liliaceae. For example, aloe extracts and processed forms of aloe for use with the invention may be obtained from *aloe arbrorescens, aloe barbandensis,* or *aloe ferox* species of aloe. Any part of the plant may be processes or extracted, such as the leaf, stem, or flower. Examples of suitable aloe compositions include *aloe arbrorescens* leaf extract (Maruzen Pharmaceuticals, Morristown, N.J.); *aloe barbandensis* leaf extract (Florida Food Products, Inc., Eustis, Fla.); *aloe barbandensis* flower extract (Tri-K, Industries, Emerson, N.J.); *aloe barbandensis* gel (Active Organics, Dallas, Tex.); and *aloe ferox* leaf extract (Maruzen Pharmaceuticals, Morristown, N.J.). The preferred aloe composition for use with the invention is *aloe barbandensis* gel, which is the fresh mucilaginous gel obtained from the parenchymatous tissue in the leaf center—referred to herein as "aloe-vera gel".

As used herein, the term "local anesthetic" means any drug that provides local numbness or analgesia or any drug that provides a regional blockage of nociceptive pathways (afferent and/or efferent). The local anesthetic can be any local anesthetic known or to be developed. Examples of local anesthetics suitable for use with the invention include: ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, or a pharmaceutically acceptable salt thereof, or a mixture thereof.

The amide and ester type local anesthetics are preferred. Amide type local anesthetics are characterized by an amide functionality, while ester type local anesthetics contain an ester functionality. Preferred amide type local anesthetics are: lidocaine, bupivacaine, prilocaine, mepivacaine, etidocaine, ropivacaine, dibucaine, and mixtures thereof. Preferred ester type local anesthetics are: tetracaine, procaine, benzocaine, chloroprocaine, their pharmaceutically acceptable salt, or a mixture thereof. The most preferred local anesthetic is lidocaine.

The meaning of "local anesthetic" also encompasses drugs not traditionally associated with local anesthetic properties but which have a local anesthetic effect, for example, non-narcotic analgesics, such as, acetylsalicylic acid, ketoprofen, piroxicam, diclofenac, indomethacin, ketorolac, Vioxx®, and Celebrex®; narcotic and opioid analgesics, such as alfentanil, allylprodine, alphaprodine, anileridine, benzylmorphine, benzitramide, buprenorphine, butorphanol, clonitazene, codeine, desomorphine, dextromoramide, dezocine, diampromide, dihydrocodeine, dihydrocodeine enol acetate, dihydormorphine, dimenoxadol, dimenoxadol, dimepheptanol, dimethylthiambutene, dioxaphetyl butyrate, dipipanone, eptazocine, ethoheptazine, ethylmethylthiambutene, etonitazene, fentanyl, hydrocodone, hydromorphone, hydroxypethidine, isomethadone, ketobemidone, levorphanol, lofentanil, meperidine, meptazinol, metazocaine, methadone, metopon, morphine, myrophine, nalbuphine, narceine, nicomorphine, norlevorphanol, normethadone, normorphine, norpipanone, opium, oxycodone, oxymorphine, papaveretum, pentazocine, phenadoxone, phenazocine, phenoperidine, piminodine, pirtramide, proheptazine, promedol, propiram, propoxyphene, remifentanil, sufentanil, tilidine, and pharmaceutically acceptable salts thereof, or mixtures thereof. For example see U.S. Pat. No. 5,589,480 (e.g., morphine or morphine sulfate), and others.

Furthermore, in order to improve the effectiveness and tolerance of the present topically effective therapy, local anesthetics with different pharmacodynamics and pharmacokinetics may be combined in a pharmaceutically acceptable topical formulation. A preferred combination of local anesthetics is lidocaine and prilocaine and another preferred combination is lidocaine and tetracaine.

The phrase "pharmaceutically acceptable salt(s)", as used herein, unless otherwise indicated, means those salts that retain the biological effectiveness and properties of neutral local anesthetics and that are not otherwise unacceptable for pharmaceutical use. Pharmaceutically acceptable salts include salts of acidic or basic groups, which groups may be present in the local anesthetics. The local anesthetics used in present invention that are basic in nature are capable of forming a wide variety of salts with various inorganic and organic acids. Pharmaceutically acceptable acid addition salts of basic local anesthetics used in the present invention are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. The local anesthetics of the present invention that include an amino moiety may form pharmaceutically acceptable salts with various amino acids, in addition to the acids mentioned above. Suitable base salts are formed from bases which form non-toxic salts and examples are the aluminium, calcium, lithium, magnesium, potassium, sodium, zinc and diethanolamine salts. For a review on pharmaceutically acceptable salts see Berge et al., *J. Pharm. Sci.,* 66, 1–19 (1977), incorporated herein by reference.

According to the present invention, any combination of an aloe composition and a triglyceride may be used, for example, a mixture of soybean oil and aloe-vera gel.

The intradermal-penetration agent/local anesthetic combination of the invention may be administered via a topical formulation or via a patch comprising the topical formulation. Preferably, the topical formulations and patch systems provide controlled release of the local anesthetic into the dermis.

In one embodiment of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g, hypotonic or buffered saline) or any other carrier known in the art for topically administering pharmaceuticals. A more complete listing of art-known carriers is provided by reference texts that are standard in the art, for example, *Remington's Pharmaceutical Sciences,* 16th Edition, 1980 and 17th Edition, 1985, both published by Mack Publishing Company, Easton, Pa., the disclosures of which are incorporated herein by reference in their entireties.

The topical formulations according to the invention may comprise excipients. Any pharmaceutically acceptable excipient is suitable. Examples of excipients that can be included in the topical formulation of the invention include, but are not limited to, preservatives, antioxidants, moisturizers, emollients, buffering agents, solubilizing agents, other penetration agents, skin protectants, surfactants, and propellants, conventional systemic pain relief therapies and analgesics, and pharmaceuticals.

Suitable preservatives include, but are not limited to, alcohols, quaternary amines, organic acids, parabens, and phenols.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerine, sorbitol, polyethylene glycols, urea, and propylene glycol.

Suitable buffering agents for use with the invention include, but are not limited to, citric, hydrochloric, and lactic acid buffers.

Suitable solubilizing agents include, but are not limited to, quaternary animonium chlorides, cyclodextrins, benzyl benzoate, lecithin, and polysorbates.

Penetration agents for use with the invention include, but are not limited to, ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methyl pyrrolidone.

Suitable skin protectants that can be used in the topical formulations of the invention include, but are not limited to, vitamin E oil, allatoin, dimethicone, glycerin, petrolatum, and zinc oxide.

The topical formulations of the invention may include medicinal agents or their pharmaceutically acceptable salts, for example, but not limited to, antifungals such as ciclopirox, chloroxylenol, triacetin, sulconazole, nystatin, undecylenic acid, tolnaftate, miconizole, clotrimazole, oxiconazole, griseofulvin, econazole, ketoconazole, and amphotericin B; antibiotics, such as mupirocin, erthromycin, clindamycin, gentamicin, polymyxin, bacitracin, and silver sulfadiazine; antiseptics, such as iodine, povidine-iodine, benzalkonium chloride, benzoic acid, chlorhexidine, nitrofurazone, benzoyl peroxide, hydrogen peroxide, hexachlorophene, phenol, resorcinol, and cetylpyridinium chloride; and anti-inflammatories, such as hydrocortisone, prednisone, triamcilolone, betamethasone, dexamethasone.

In yet another embodiment of the current invention, agents may be included in the topical formulation to prolong the local anesthetic effect, such as, a glucocorticosteroid (see, U.S. Pat. No. 5,922,340, incorporated herein by reference) or a vasoconstrictor, such as a catecolamine.

The topical formulation of the invention may be applied to the skin of a subject via a container adapted for spraying. After application of the topical formulation to the epidermis, the area may be covered with a dressing. The term "dressing", as used herein, means a covering designed to protect a topically applied drug formulation. "Dressing" includes coverings such as a bandage, which may be porous or non-porous and various inert coverings, e.g., a plastic film wrap or other non-absorbent film. The term "dressing" also encompasses non-woven or woven coverings, particularly elastomeric coverings, which allow for heat and vapor transport. These dressings allow for cooling of the treated area, which provides for greater comfort.

In a preferred embodiment of the current invention, the topical formulation comprising a local aesthetic and an intradermal-penetration agent is contained in a patch that is applied adjacent to the area of skin to be treated. As used herein a "patch" comprises at least a topical formulation and a covering layer, such that, the patch can be placed over the area of skin to be treated. Preferably, the patch is designed to maximize drug delivery through the stratum corneum and into the epidermis or dermis, and to minimize absorption into the circulatory system, reduce lag time, promote uniform absorption, and reduce mechanical rub-off.

Preferably, the patch components resemble the viscoelastic properties of the skin and conform to the skin during movement to prevent undue shear and delamination.

A patch comprising the topical formulation of the invention has advantages over conventional methods of administration. One advantage is that the dose is controlled by the patch's surface area. Other advantages of patches are constant rate of administration, longer duration of action (the ability of to adhere to the skin for 1, 3, 7 days or longer); improved patient compliance, non-invasive dosing, and reversible action (i.e., the patch can simply be removed).

A patch suitable for use with the invention should contain at least: (1) a backing layer and (2) a carrier formulated with a local anesthetic.

Preferred patches include (1) the matrix type patch; (2) the reservoir type patch; (3) the multi-laminate drug-in-adhesive type patch; and (4) the monolithic drug-in-adhesive type patch; and (Ghosh, T. K.; Pfister, W. R.; Yum, S. I. *Transdermal and Topical Drug Delivery Systems,* Interpharm Press, Inc. p. 249–297, incorporated herein by reference). These patches are well known in the art and generally available commercially.

For practice of the invention, the matrix type and the drug-in-adhesive type patches are especially preferred. The more preferred drug-in-adhesive patch is the monolithic type.

The matrix patch comprises an anesthetic containing matrix, an adhesive backing film overlay, and preferably, a release liner. In some cases, it may be necessary to include a impermeable layer to minimize drug migration into the backing film (e.g., U.S. Pat. No. 4,336,243, incorporated herein by reference). The anesthetic containing matrix is held against the skin by the adhesive overlay. Examples of suitable anesthetic matrix materials include but are not limited to lipophilic polymers, such as polyvinyl chloride, polydimethylsiloxane, and hydrophilic polymers like polyvinylpyrrolidone, polyvinyl alcohol, hydrogels based on gelatin, or polyvinylpyrrolidone/polyethylene oxide mixtures.

The reservoir type patch design is characterized by a backing film coated with an adhesive, and a reservoir compartment comprising a drug formulation preferably, in the form of a solution or suspension, that is separated from the skin by a semipermeable membrane (e.g., U.S. Pat. No. 4,615,699, incorporated herein by reference). The adhesive coated backing layer extends around the reservoir's boundaries to provide a concentric seal with the skin and hold the reservoir adjacent to the skin.

The monolithic drug-in-adhesive patch design is characterized by the inclusion of the drug formulation in the skin contacting adhesive layer, a backing film and preferably, a release liner. The adhesive functions both to release the anesthetic and adhere the anesthetic matrix to the skin. The drug-in-adhesive system does not require an adhesive overlay and thus the patch size is minimized. Also, drug-in-adhesive type patches are thin and comfortable (e.g., U.S. Pat. No. 4,751,087, incorporated herein by reference).

The multi-laminate drug-in-adhesive patch design further incorporates an additional semi-permeable membrane between two distinct drug-in-adhesive layers or multiple drug-in-adhesive layers under a single backing film (Peterson, T. A. and Dreyer, S. J. Proceed. *Intern. Symp. Control. Rel. Bioact. Mater.* 21: 477–478, incorporated herein by reference).

Semi permeable membranes, useful with the reservoir or multi-laminate patch, include thin non-porous ethylene vinyl acetate films or thin microporous films of polyethylene employed in microlaminate solid state reservoir patches. Adhesives for use with the drug-in-adhesive type patches are well known in the art and selection is readily accomplished by an ordinary practitioner. Three basic types commonly used are polyisobutylenes, silicones, and acrylics. Adhesives useful in the present invention can function under a wide range of conditions, such as, high and low humidity, bathing, sweating etc. Preferably the adhesive is a composition based on natural or synthetic rubber; a polyacrylate such as, polybutylacrylate, polymethylacrylate, poly-2-ethylhexyl acrylate; polyvinylacetate; polydimethylsiloxane; or and hydrogels (e.g., high molecular weight polyvinylpyrrolidone and oligomeric polyethylene oxide). The most preferred adhesive is a pressure sensitive acrylic adhesive, for example Durotak® adhesives (e.g., Durotak® 2052, National Starch and Chemicals). The adhesive may contain a thickener, such as a silica thickener (e.g., Aerosil, Degussa, Ridgefield Park, N.J.) or a crosslinker such as, aluminumacetylacetonate.

Suitable release liners include but are not limited to occlusive, opaque, or clear polyester films with a thin coating of pressure sensitive release liner (e.g., silicone-fluorsilicone, and perfluorcarbon based polymers.

Backing films may be occlusive or permeable and are derived from synthetic polymers like polyolefin oils polyester, polyethylene, polyvinylidine chloride, and polyurethane or from natural materials like cotton, wool, etc. Occlusive backing films, such as synthetic polyesters, result in hydration of the outer layers of the stratum corneum while non-occlusive backings allow the area to breath (i.e., promote water vapor transmission from the skin surface). More preferably the backing film is an occlusive polyolefin foil (Alevo, Dreieich, Germany). The polyolefin foil is preferably about 0.6 to about 1 mm thick.

A particularly preferred patch design comprises a polyolefin foil and a pressure sensitive acrylic adhesive comprising the active agents and any excipients.

Additionally, in order to make the present therapy safer, use-specific, and more manageable overall, the present patch may have such a geometric shape such that it corresponds to the special conditions of the application field. Thus, the shape of the patch can be flat or three-dimensional, round, oval, square, and have concave or convex outer shapes, or the patch or bandage can also be segmented by the user into corresponding shapes with or without additional auxiliary means.

Selection of the appropriate dosage for the application site is an important consideration. The rate of intradermal anesthetic administration from the topical formulation or patch is a function of skin permeability, and skin permeability has been shown to vary between anatomical sites depending on the thickness of the stratum corneum. For example, the permeability, in general, increases in order from planter foot arch, lateral ankle, palm, ventral forearm, dorsal forearm, back, chest, thigh, abdomen, scalp, axilla, forehead, and scrotum (Wester, R. C. and Maibach, H. I. (1989) Regional variation in Percutaneous Absorption: In *Percutaneous Absorption, Mechanism, Methodology, Drug Delivery*, $2^{nd}$ ed., Eds. R. L. Bronaugh and H. I. Maibach, Marcel Dekker, Inc., New York, pp. 111–119 (incorporated herein by reference)). Of course, the dosages and dosing frequency will be determined by a trained medical professional.

The amount of local anesthetic in the topical formulation will generally be of from about 1 percent to about 25 percent of the total weight of the formulation, preferably, of from about 2 percent to about 20 percent, more preferably, of from about 3 percent to about 6 percent of the total weight of the formulation.

When a combination of local anesthetics is used, a preferred combination is a eutectic mixture of lidocaine and prilocaine. In such a mixture, the amount of lidocaine can range of from about 0.5 percent to about 12 percent, preferably of from about 1 percent to about 7 percent, and more preferably of from about 2.5 percent to about 5 percent and the amount of prilocaine can range of from about 0.5 percent to about 12 percent, preferably of from about 1 percent to about 7 percent, and more preferably of from about 2.5 percent to about 5 percent. Preferably, the mixture is formulated as an oil in water emulsion.

Another preferred local aesthetic combination is a mixture of lidocaine and tetracaine. In such a mixture, the amount of lidocaine can range of from about 0.5 percent to about 12 percent, preferably of from about 1 percent to about 7 percent, and more preferably of from about 2.5 percent to about 5 percent and the amount of tetracaine can range of from about 0.5 percent to about 12 percent, preferably of from about 1 percent to about 7 percent, and more preferably of from about 2.5 percent to about 5 percent. Preferably the mixture is formulated as an oil in water emulsion.

The amount of intradermal-penetration agent in the topical formulation will generally be of from about 1 percent to about 90 percent of the total weight of the formulation, preferably, of from about 2 percent to about 50 percent, more preferably, of from about 3 percent to about 10 percent of the total weight of the formulation.

The intradermal-dermal penetration agent present in the topical formulation of the invention can comprise a mixture of a triglyceride, (e.g., soybean oil) and an aloe composition (e.g., aloe-vera gel). When such a mixture is used, the triglyceride can be present in an amount of from about of from about 0.5 percent to about 45 percent of the total weight of the formulation, preferably, of from about 1 percent to about 25 percent, more preferably, of from about 1.5 percent to about 5 percent of the total weight of the formulation and the aloe composition can be present in an amount of from about 0.5 percent to about 45 percent of the total weight of the formulation, preferably, of from about 1 percent to about 25 percent, more preferably, of from about 1.5 percent to about 5 percent of the total weight of the formulation.

With gels, creams, or ointments, typically 1 to 4 applications are required per day. Generally, about 0.5 $g/cm^2$ to about 5 $g/cm^2$, preferably 1 $g/cm^2$ to about 2 $g/cm^2$ of the topical formulation is applied to the epidermis. Preferably, the formulation is applied to the skin area in an amount of from about 1 g/cm² to about 2 g/cm². Preferably, after application, the treated area is covered with a dressing.

When a patch is used to achieve a local anesthetic effect, the local anesthetic required is determined by the active surface area of the medicated portion of the patch in direct contact with the skin. Several dosage strengths are advantageous depending upon the condition to be treated. In general, a physician may begin dosing with a low or intermediate strength patch and then, depending upon the effectiveness, adjust the dosage up or down by prescribing a patch of higher or lower anesthetic concentration or a patch of larger or smaller surface area, or, in some cases, multiple patches.

Preferably, the local anesthetic in the patch will comprise of from about 0.5 percent to about 40 percent by weight of the patch's total weight, preferably of from about 10 percent to about 30 percent, more preferably of from about 15 percent to about 25 percent, and most preferably of from about 18 percent to about 22 percent by weight of the patch's total weight.

When a combination of local anesthetics is used in the patch, a preferred combination is a eutectic mixture of lidocaine and prilocaine. In such a mixture, the amount of lidocaine can range of from about 0.25 percent to about 20 percent, preferably of from about 1 percent to about 15 percent, and more preferably of from about 2 percent to about 10 percent and the amount of prilocaine can range of from about 0.25 percent to about 20 percent, preferably of from about 1 percent to about 15 percent, and more preferably of from about 2 percent to about 10 percent.

Another preferred local aesthetic combination for use in a patch is a mixture of lidocaine and tetracaine. In such a mixture, the amount of lidocaine can range of from about 0.25 percent to about 20 percent, preferably of from about 1 percent to about 15 percent, and more preferably of from about 2 percent to about 10 percent and the amount of tetracaine can range of from about 0.25 percent to about 20 percent, preferably of from about 1 percent to about 15 percent, and more preferably of from about 2 percent to about 10 percent.

In general, the intradermal-penetration agent will comprise of from about 0.5 percent to about 40 percent by weight of the patch's total weight, preferably of from about 2 percent to about 20 percent, more preferably of from about 3 percent to about 6 percent by weight of the patch's total weight.

The intradermal-dermal penetration agent present in patch of the invention can comprise a mixture of a triglyceride, (e.g., soybean oil) and an aloe composition (e.g., aloe-vera gel). When such a mixture is used, the triglyceride can be present in an amount of from about of from about 0.25 percent to about 25 percent of the total weight of the patch, preferably, of from about 0.5 percent to about 12 percent, more preferably, of from about 1 percent to about 5 percent of the total weight of the patch and the aloe composition can be present in an amount of from about 0.25 percent to about 25 percent of the total weight of the patch, preferably, of from about 0.5 percent to about 12 percent, more preferably, of from about 1 percent to about 5 percent of the total weight of the patch.

The intradermal-penetration agent/local anesthetic combination of the invention may be used to treat conditions conventionally treated by topical application of local anesthetics. For example, the invention is useful for treating minor skin abrasions and cuts, insect bites, headaches, back pain, or any pain or condition caused by stimulation of sub-dermal sensory nerve receptors (i.e., nociceptors) or that can be treated by regional blockage of nociceptive pathways (afferent and/or efferent). The invention may also be used to for local anesthetization of skin prior to a minor surgical procedure such as an injection. Fresh patches may be applied multiple times per day, depending on the condition treated and a physician's recommendation. In general, a fresh patch is applied about every 18 to about every 48 hours. More preferably, the patch is applied daily.

Although the present invention has been described in considerable detail with reference to certain preferred embodiments, other embodiments are possible. Therefore, the spirit and scope of the appended claims should not be limited to the description of the preferred embodiments contained herein.

EXAMPLES

The following examples are provided for illustrative purposes only and are not to be construed as limiting the invention's scope in any manner.

Example 1

Comparison of Aloe-Vera Gel with Propylene Glycol as an Intradermal-Penetration Agent The study was conducted with a 10 cm² matrix patch composed of 1 mm thick polyolefin foam (as an occlusive backing) coated with an acrylate matrix, the matrix comprising a mixture of lidocaine and intradermal-penetration agent in an acrylate polymer.

The matrix was prepared by mixing lidocaine (20 weight percent); acrylate polymer (Durotak® 387–2052, 75 weight percent); intradermal-penetration agent; aluminumacetylacetonate ($Al(ACAC)_3$, 0.4 weight percent, as a crosslinker); and ethanol until homogeneous. Note, that a greater weight of propylene glycol than aloe-vera gel accounts for propylene glycol's higher evaporation rate. The homogeneous mixture was then coated on polyolefin foil with a hand-coater machine to an average thickness of about 270 µm. The coated foil was dried for about 1 hour at about 50° C. to evaporate the ethanol giving the patch. The average patch weight was 50 g/m² dry. The amounts of lidocaine and intradermal-penetration agent in each patch are given in the Table I below as the percentage of the total patch weight.

The matrix patch was applied to the forearm of 8 volunteers. The volunteers assumed normal activities including bathing during which all of the patches adhered reliably throughout the study. After 24 hours, the patches were removed. All eight volunteers reported a local anesthetic effect up to 5 hours from the patch removal time. Immediately after patch removal, each of the eight volunteers' patches was extracted with an organic solvent to extract the residual lidocaine and the weight of lidocaine remaining in each patch was measured by HPLC analysis. The mean rate of intradermal lidocaine penetration into the volunteer's forearms was calculated in mg/day as the initial lidocaine weight less the weight of lidocaine remaining in the patch after the study, as determined by HPLC, averaged over the 8 volunteers.

TABLE I

Amounts of lidocaine and intradermal-penetration agent
in each patch and penetration data

| No. | weight % of lidocaine | intradermal-penetration agent | intradermal-penetration agent concentration | Mean intradermal skin penetration rate (mg/day) |
|---|---|---|---|---|
| 1 | 20% | aloe-vera gel | 10% | 26 |
| 2 | 24% | aloe-vera gel | 7.5% | 28 |
| 3 | 20% | propylene glycol | 20% | 18 |

The penetration-rate data in Table I above indicates that aloe-vera gel is superior to propylene glycol as a intradermal-penetration agent.

Example 2
Comparison of Soybean Oil with Propylene Glycol as an Intradermal-Penetration Agent.

A 10 cm$^2$ matrix patch composed of 1 mm thick polyolefin foam coated with an acrylate matrix, the matrix comprising a mixture of lidocaine and intradermal-penetration agent in an acrylate polymer was prepared as in Example 1. A thickener (3 weight percent Aerosil) was included in formulation 1. The amounts of lidocaine and intradermal-penetration agent in each patch are given in the Table II below as the percentage of the total patch weight.

The patch was placed on a piece of nude mouse skin, with a larger area than the patch's area, and the lower surface of the mouse skin was contacted with physiologic phosphate buffer for 24 hours. The weight of lidocaine in the buffer solution was determined by quantitative HPLC analysis as above. The intradermal rate of absorption per unit area was then calculated as the weight of lidocaine in the buffer solution divided by the patch's surface area. Three measurements were determined for each formulation and the values averaged.

TABLE II

Amounts of lidocaine and intradermal-penetration agent
in each patch and penetration data

| formulation | wt. % lidocaine | intradermal-penetration agent | intradermal-penetration agent concentration | Intradermal skin penetration $\mu g/cm^2$/24 hours | Adhesive properties |
|---|---|---|---|---|---|
| 1 | 20% | Propylene glycol | 20 | not detected | too high |
| 2 | 20% | soybean oil | 5 | 1000 | good |

The penetration-rate data in Table II above indicates that soybean oil is superior to propylene glycol as a intradermal-penetration agent.

The foregoing has outlined rather broadly the more pertinent and important features of the present invention. While it is apparent that the invention disclosed herein is well calculated to fulfill the objects stated above, it will be appreciated that numerous modifications and embodiments may be devised by those skilled in the art. Therefore, it is intended that the appended claims cover all such modifications.

What is claimed is:

1. A patch comprising a backing and an adhesive, which adhesive comprises a penetration enhancing amount of soybean oil and a therapeutically effective amount of a local anesthetic.

2. The patch of claim 1, wherein the local anesthetic is one or more of lidocaine, tetracaine, bupivacaine, prilocaine, mepivacaine, procaine, chloroprocaine, ropivacaine, dibucaine, etidocaine, benzocaine, and a pharmaceutically acceptable salt thereof.

3. The patch of claim 1, further comprising an aloe composition.

4. The patch of claim 2, wherein the aloe composition is aloe vera gel.

5. The patch of claim 1, wherein the backing comprises a polyolefin, polyester, polyvinylidine chloride, polyurethane, cotton, or wool.

6. The patch of claim 1, wherein the backing comprises a polyolefin foil.

7. The patch of claim 6, wherein the polyolefin foil has a thickness of from about 0.6 mm to about 1.0 mm.

8. The patch of claim 1, wherein the adhesive comprises a polyisobutylene, a silicone, an acrylic, or a mixture thereof.

9. The patch of claim 8, wherein the adhesive comprises a pressure sensitive acrylic.

10. The patch of claim 8, wherein the adhesive comprises a polyacrylate.

11. The patch of claim 10, wherein the polyacrylate is polybutylacrylate, polymethylacrylate, or poly-2-ethylhexylacrylate.

* * * * *